United States Patent
Liang et al.

(10) Patent No.: US 12,195,754 B2
(45) Date of Patent: Jan. 14, 2025

(54) CELL DIFFERENTIATION MEDIUM COMPOSITION, HIGH SECRETION INSULIN-PRODUCING CELLS AND PREPARATION METHOD THEREOF

(71) Applicant: Gwo Xi Stem Cell Applied Technology Co., Ltd., Zhubei (TW)

(72) Inventors: Ruei-Yue Liang, Zhubei (TW); Kai-Ling Zhang, Zhubei (TW); Ming-Hsi Chuang, Zhubei (TW); Po-Cheng Lin, Zhubei (TW); Chun-Hung Chen, Zhubei (TW); Pei-Syuan Chao, Hsinchu (TW)

(73) Assignee: Gwo Xi Stem Cell Applied Technology Co., Ltd., Zhubei (TW)

( * ) Notice: Subject to any disclaimer, the term of this patent is extended or adjusted under 35 U.S.C. 154(b) by 542 days.

(21) Appl. No.: 17/235,910

(22) Filed: Apr. 20, 2021

(65) Prior Publication Data
US 2021/0371812 A1    Dec. 2, 2021

Related U.S. Application Data

(60) Provisional application No. 63/031,596, filed on May 29, 2020.

(30) Foreign Application Priority Data

Jan. 25, 2021 (TW) .................. 110102610

(51) Int. Cl.
*C12N 5/00* (2006.01)
*C12N 5/071* (2010.01)

(52) U.S. Cl.
CPC ......... *C12N 5/0037* (2013.01); *C12N 5/0678* (2013.01); *C12N 2500/02* (2013.01); *C12N 2500/32* (2013.01); *C12N 2500/34* (2013.01); *C12N 2500/38* (2013.01); *C12N 2500/90* (2013.01); *C12N 2501/12* (2013.01); *C12N 2501/16* (2013.01); *C12N 2501/998* (2013.01); *C12N 2506/1353* (2013.01); *C12N 2506/1369* (2013.01); *C12N 2506/1384* (2013.01)

(58) Field of Classification Search
CPC ................ C12N 5/0037; C12N 5/0678; C12N 2501/12; C12N 2501/16; C12N 2501/998; C12N 2506/1353; C12N 2506/1369; C12N 2506/1384
See application file for complete search history.

(56) References Cited

PUBLICATIONS

Hald et al., (2011) Pancreatic islet and progenitor cell surface markers with cell sorting potential. Diabetologia, 55, 154-165 (Year: 2011).*
Cheng et al., (2011) Human adipose-derived stem cells: Isolation, characterization and current application in regeneration medicine. Genomic Medicine, Biomarkers, and Health Sciences, 3(2), 53-62 (Year: 2011).*
Timper et al., (2006) Human adipose tissue-derived mesenchymal stem cells differentiate into insulin, somatostatin, and glucagon expressing cells. Biochemical and Biophysical Research Communications, 341(4), 1135-1140 (Year: 2006).*
Lin et al., (2005) Accelerated growth and prolonged lifespan of adipose tissue-derived human mesenchymal stem cells in a medium using reduced calcium and antioxidants. Stem Cells and Development, 14, 92-102 (Year: 2005).*
Liu et al., (2017) Chitosan-assisted differentiation of porcine adipose tissue-derived stem cells into glucose-responsive insulin-secreting clusters. PLoS One DOI: 10.1371/journal.pone.0172922 (Year: 2017).*

* cited by examiner

*Primary Examiner* — Kara D Johnson

(57) ABSTRACT

The present invention relates to a cell differentiation medium composition, a high secretion insulin-producing cells and a preparation method thereof. The high secretion insulin-producing cells obtained by using the cell differentiation medium composition to induce stem cell differentiated under specific conditions can secrete a large amount of insulin in a short time, and when the high-secreting insulin-producing cells are transplanted into the human body, they are not easy to be swallowed by macrophages, which can improve the survival rate of the insulin-producing cells and prolong the time of insulin secretion thereby.

5 Claims, 5 Drawing Sheets

Specification includes a Sequence Listing.

SEQUENCE LISTING

<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: Forward primer for Ipf-1

<400> SEQUENCE: 1
tgatactgga ttggcgttgt tt                                              22

<210> SEQ ID NO 2
<211> LENGTH: 21
<212> TYPE: DNA
<213> ORGANISM: Artificial Sequence
<220> FEATURE:
<223> OTHER INFORMATION: Reverse primer for Ipf-1

<400> SEQUENCE: 2
tcccaaggtg gagtgctgta g                                               21

<210> SEQ ID NO 3
<211> LENGTH: 24
<212> TYPE: DNA
<213> ORGANISM: Artificial Sequence
<220> FEATURE:
<223> OTHER INFORMATION: Forward primer for Isl-1

-continued

```
<400> SEQUENCE: 3
caactggtca atttttcaga agga                                          24

<210> SEQ ID NO 4
<211> LENGTH: 26
<212> TYPE: DNA
<213> ORGANISM: Artificial Sequence
<220> FEATURE:
<223> OTHER INFORMATION: Reverse primer for Isl-1

<400> SEQUENCE: 4
ttgagaggac attgatgcta cttcac                                        26

<210> SEQ ID NO 5
<211> LENGTH: 20
<212> TYPE: DNA
<213> ORGANISM: Artificial Sequence
<220> FEATURE:
<223> OTHER INFORMATION: Forward primer for Insulin

<400> SEQUENCE: 5
gcagcctttg tgaaccaaca                                               20

<210> SEQ ID NO 6
<211> LENGTH: 22
<212> TYPE: DNA
<213> ORGANISM: Artificial Sequence
<220> FEATURE:
<223> OTHER INFORMATION: Reverse primer for Insulin

<400> SEQUENCE: 6
ttccccgcac actaggtaga ga                                            22

<210> SEQ ID NO 7
<211> LENGTH: 20
<212> TYPE: DNA
<213> ORGANISM: Artificial Sequence
<220> FEATURE:
<223> OTHER INFORMATION: Forward primer for CD47

<400> SEQUENCE: 7
ggcaatgacg aaggaggtta                                               20

<210> SEQ ID NO 8
<211> LENGTH: 20
<212> TYPE: DNA
<213> ORGANISM: Artificial Sequence
<220> FEATURE:
<223> OTHER INFORMATION: Reverse primer for CD47

<400> SEQUENCE: 8
atccggtggt atggatgaga                                               20

<210> SEQ ID NO 9
<211> LENGTH: 25
<212> TYPE: DNA
<213> ORGANISM: Artificial Sequence
<220> FEATURE:
<223> OTHER INFORMATION: Forward primer for HPRT

<400> SEQUENCE: 9
tcaggcagta taatccaaag atggt                                         25

<210> SEQ ID NO 10
```

```
<211> LENGTH: 25
<212> TYPE: DNA
<213> ORGANISM: Artificial Sequence
<220> FEATURE:
<223> OTHER INFORMATION: Reverse primer for HPRT

<400> SEQUENCE: 10
agtctggctt atatccaaca cttcg                                            25
```

CELL DIFFERENTIATION MEDIUM COMPOSITION, HIGH SECRETION INSULIN-PRODUCING CELLS AND PREPARATION METHOD THEREOF

CROSS REFERENCE TO RELATED APPLICATIONS

The present application claims the benefit of Taiwanese Patent Application No. 110102610 filed on Jan. 25, 2021 and U.S. Provisional application No. 63/031,596 filed on May 29, 2020. The contents of the above-identified applications are incorporated herein by reference in their entirety.

REFERENCE TO SEQUENCE LISTING

The Substitute Sequence Listing is submitted to replace the previously submitted sequence listing as an ASCII formatted text filed via EFS-Web, with a file name of "Substitute_Sequence_Listing_WTOIP-21005-USPT.TXT", a creation date of May 11, 2021, and a size of 2,301 bytes. The Substitute Sequence Listing filed via EFS-Web is part of the specification and is incorporated in its entirety by reference herein.

BACKGROUND OF THE INVENTION

Technical Field

The present invention relates to a cell differentiation medium, and a method of differentiating stem cells by using the cell differentiation medium. In particular, the present invention relates to a preparation method for differentiating stem cells into high secretion insulin-producing cells.

Background

Diabetes is an endocrine disease which is due to either pancreas not producing enough insulin or the body of the patient is failure to effectively use insulin. It destroys the regulation of blood glucose, so that the blood glucose in the patient is too high. Based on the pathogenesis, the mainly types of diabetes are Type 1 diabetes, Type 2 diabetes and Gestational diabetes. If left untreated, high blood glucose leads to problems such as cardiovascular disease, stroke, chronic kidney disease, foot ulcers, damage to the nerves, damage to the eyes and cognitive impairment.

Prevention and treatment for diabetes involve, especially for Type 2 diabetes, maintaining a healthy diet, regular physical exercise, a normal body weight, and avoiding use of tobacco. Type 1 diabetes must be managed with insulin injections. Type 2 is largely preventable by staying a normal weight, exercising regularly, and eating properly. However, many patients may eventually also require insulin injections. Furthermore, Gestational diabetes usually resolves after the birth of the baby.

In recent years, some researchers have differentiated mesenchymal stem cells into insulin-producing cells based on the characteristics of mesenchymal stem cells being capable of differentiating into variety of cell types, and injected them into animal for diabetes treatment. In addition, in order to make the characteristics of the insulin-producing cells similar to those of real pancreatic islet B cells, the mesenchymal stem cells mainly to be differentiated into spheroid or clump-like cells.

However, there are still some challenges that must be overcome to culture sphere or clump-like cells, such as the sizes of sphere or clump-like cells, control of the cell count, the need for multiple steps in the purification process and the need for special scaffolds or materials, which will increase the manufacturing cost. In addition, the size of the sphere or clump will affect the oxygen content of the central cell, which is likely to cause internal cells death.

SUMMARY OF THE INVENTION

Therefore, the applicant provides a cell differentiation medium composition and a new differentiation method to solve the above-mentioned problem, which is able to further increase the insulin secretion of the insulin-producing cells and the survival rate of the insulin-producing cells in the organism.

That is, an object of the present invention is to provide a cell differentiation medium composition which is a serum-free DMEM/F12 medium comprising at least glucose, nicotinamide, activin-A, exendin-4, hepatocyte growth factor, pentagastrin, a B-27™ Serum-Free Supplement (Gibco), and a N-2 Supplement, and the cell differentiation medium composition is antibiotic-free.

In a particular embodiment, the cell differentiation medium composition is a serum-free DMEM/F12 medium comprising at least 5~25 mM glucose, 5~15 mM nicotinamide, 1~10 μM activin-A, 5~20 nM exendin-4, 80~120 fM hepatocyte growth factor (HGF), 5~20 nM pentagastrin, 0.1~5% B-27™ Serum-Free Supplement (Gibco), and 0.1~5% N-2 Supplement.

Further, another object of the present invention is to provide a preparation method for a high secretion insulin-producing cells, which comprises: (a) cell attachment step: pour a solution containing stem cells into a cell culture container and let stand for at least 24 hours for cell attachment, so that the quantity of stem cells attached to the peripheral wall of the culture container is in a range of 6,000 and 15,000 cells/cm$^2$; preferably in a range of 6,000 to 12,000 cells/cm$^2$; more preferably in a range of 6,000 to 10,000 cells/cm$^2$; most preferably in a range of 6,000 to 8,000 cells/cm$^2$; (b) cell differentiation step: removing the solution from the culture container, putting the aforementioned cell differentiation medium composition into the culture container, inducing the stem cells into high-secreting insulin-producing cells under the conditions of an ambient temperature of 35.5~39.5° C. and a $CO_2$ concentration of 5%, and then collecting the high-secreting insulin-producing cell after differentiating for at least 2 days ( According to a specific embodiment of the present invention, before the cell attachment step (a) further comprising: culturing the stem cells at least 3 days for cell proliferation by using a proliferation medium; the proliferation medium is a keratinocyte serum-free media which comprises fetal bovine serum, N-acetyl-L-cysteine, L2 ascorbic acid, and phosphate.

According to a specific embodiment of the present invention, the cell culture time in the cell differentiation step (b) is in a range of 3 to 30 days; preferably in a range of 3 to 21 days; more preferably in a range of 3 to 14 days; most preferably in a range of 3 to 7 days.

According to a specific embodiment of the present invention, the stem cell is at least one selected from the group consisting of an adipose-derived stem cell, a bone marrow stem cell, a peripheral blood stem cell, a cord blood stem cell.

According to a specific embodiment of the present invention, the insulin secretion of each 100 thousand of high secretion insulin-producing cells per day is above 1,000 mIU/L.

In addition, another object of the present invention is to provide a high secretion insulin-producing cell, and the morphology of which is spindle-shaped; the high secretion insulin-producing cell has insulin gene, IPF-1 gene ISL-1 gene and expresses the same surface markers with the stem cells, which are CD73 (positive), CD90 (positive) and CD45 (negative).

According to a specific embodiment of the present invention, wherein the express level of CD47 mRNA of the high secretion insulin-producing cell is more than 3 times that of the stem cell.

DETAILED DESCRIPTION OF THE PREFERRED EMBODIMENTS

Figure 1:
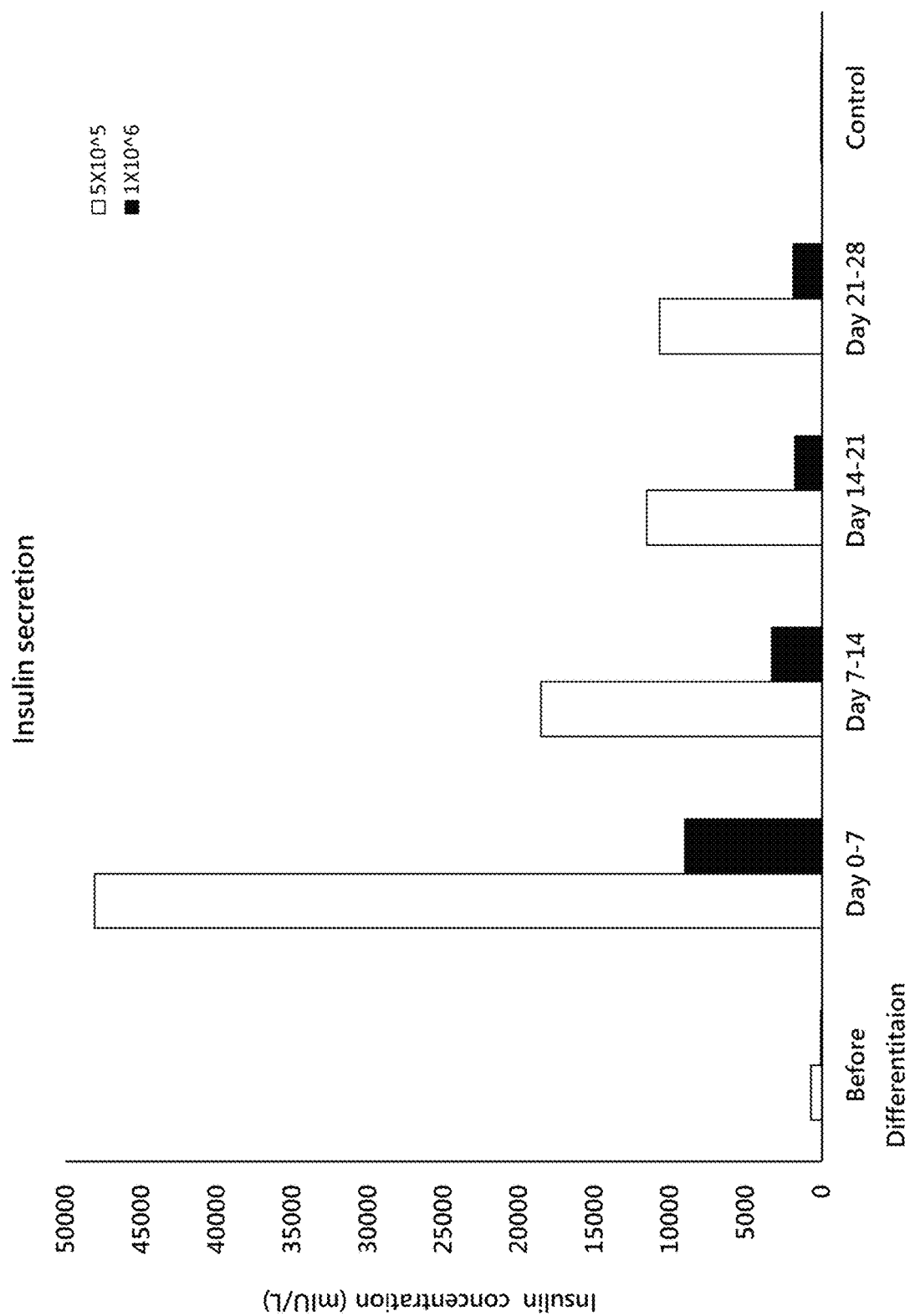
FIG. 1 is a diagram illustrating results of insulin content analysis for $5\times10^5$ hADSCs and 106 hADSCs.

In order to enable those skilled in the art to better understand the objects, technical features, and advantages of the present invention and accordingly implement the present invention, the technical features and implementations of the present invention are illustrated in detail herein in conjunction with the accompanying drawings, and preferred embodiments are exemplified for further description. The drawings referenced in the following description are schematic representations for expressing the features of the present invention, and are not and need not be drawn completely based on actual situations.

Herein, all technical and scientific terms used herein have the same meaning as commonly understood by one of ordinary skill in the art to which this invention belongs. Further, unless otherwise clearly contradicted by context, singular terms used herein shall include pluralities and plural terms shall include the singular.

Notwithstanding that the numerical ranges and parameters setting forth the broad scope of the invention are approximations, the numerical values set forth in the specific examples are presented herein as precisely as possible. Any numerical value, however, inherently contains certain errors necessarily resulting from the standard deviation found in its respective testing measurement. Herein, the term "about" generally means that an actual value is within 10%, 5%, 1%, or 0.5% above and below a particular value or range. Alternatively, the term "about" indicates that the actual value falls within an acceptable standard error of the mean when considered by one of ordinary skill in the art. Except in the Examples, or where otherwise explicitly indicated, all ranges, amounts, values, and percentages used herein (for example, for describing amounts of materials, time, temperature, operation conditions, amount ratio, and the like) are understood to be modified by the word "about". Thus, unless expressly stated to the contrary, the numerical parameters disclosed in this specification and the appended claims are all approximations and, if required, may vary. At the very least, each numerical parameter should at least be construed in light of the number of reported significant digits and by applying ordinary rounding techniques.

For a more thorough and complete description of this disclosure, illustrative description for implementation aspects and specific examples of this invention is provided below; however, this is not intended to represent the only form of specific examples in which the present invention may be practiced or utilized. Features of a number of specific examples and process steps and sequences to construct and operate these specific examples are covered in the embodiments. However, the same or equivalent functions and step sequences may also be accomplished by other examples.

<Proliferation of Human Adipose Tissue-Derived MSCs (hADSCs)>

Cells used in the embodiment were Human Adipose Tissue-Derived MSCs (hADSCs).

Adipose tissue (2-5 g) was harvested from the subcutaneous fat of the abdominal wall by lipoaspiration during abdominal surgery from healthy donors. All donors gave written informed consent. Human fat tissue was placed in $Ca^{2+}/Mg^{2+}$-free phosphate-buffered saline (PBS) and immediately transferred to the laboratory.

Human adipose tissue was removed from the transport medium, placed in a Petri dish, and cut into small pieces (1-2 $mm^3$) in the presence of $Ca^{2+}/Mg^{2+}$-free PBS. The tissues were dissociated with 0.1% collagenase I and incubated for 60 min at 37° C. After enzymatic digestion, the resultant cells were collected and cultured with a proliferation medium. The proliferation medium is a keratinocyte serum-free media (SFM) supplemented with 10% fetal bovine serum (FBS), N-acetyl-L-cysteine, L2 ascorbic acid, and phosphate. The supernatant and debris were removed from the culture dish to obtain primary hADSCs after being cultured for 2 days.

Then, in order to increase cell count, the above-mentioned primary hADSCs can be continuously cultured in a proliferation medium to the required quantity.

<Differentiation of Human Adipose Tissue-Derived MSCs (hADSCs)>

First, prepared a differentiation medium composition. The differentiation medium composition was a serum-free DMEM/F12 medium which contains 5~25 mM glucose, 5~15 mM nicotinamide, 1~10 μM activin-A, 5~20 nM exendin-4, 80~120 fM hepatocyte growth factor (HGF), 5~20 nM pentagastrin, 0.1~5% B-27™ Serum-Free Supplement (Gibco), and 0.1~5% N-2 supplement. Furthermore, the differentiation medium composition of the present invention does not contain antibiotics (such as penicillin/streptomycin solution), which can avoid affecting cell growth and changing cell surface marker. The concentration of each component in the differentiation medium composition are shown in Table 1.

TABLE 1

| Component | Concentration |
|---|---|
| Serum-Free DMEM/F12 Medium | — |
| Glucose | 5~25 mM |
| Nicotinamide | 5~15 mM |
| Activin-A | 1~10 pM |

TABLE 1-continued

| Component | Concentration |
| --- | --- |
| Exendin-4 | 5~20 nM |
| Hepatocyte Growth Factor | 80~120 fM |
| Pentagastrin | 5~20 nM |
| B-27 Serum-Free Supplement | 0.1~5% |
| N-2 Supplement | 0.1~5% |

Then, after the stem cell proliferation was completed, $5 \times 10^5$ hADSCs and $1 \times 10^6$ hADSCs were seeded respectively in T75 flasks containing the proliferation medium and incubated 24 hours for cell attachment. The attached cells were washed twice with 10 ml of the serum-free DMEM/F12 medium (the removed liquid was used for analyzing the insulin concentration of stem cells before differentiation), and 10 ml of the differentiation medium was added there to for monolayer culture.

The flasks with the seeded hADSCs were placed in a C02 incubator at 5% $CO_2$ and 35.5~39.5° C. for differentiating to obtain high secretion insulin-producing cells. The differentiation medium was replaced every 7 days, and the replaced differentiation medium was collected for insulin content analysis.

The insulin content analysis was based on Chemiluminescence (model: ADVIA CentaurXPT, SIEMENS) method, and the results were recorded in Table 2.

TABLE 2

| | | control* | example 1 | example 2 |
| --- | --- | --- | --- | --- |
| cell count in a T75 flask | | 0 | $5 \times 10^5$ | $1 \times 10^6$ |
| cell density (cells/cm$^2$) | | 0 | 6666.6 | 13333.3 |
| Insulin concentration (mIU/L) | Before Differentiation | — | 716.4 | 87 |
| | Day 0-7 | 65.8 | 48104.7 | 9034.2 |
| | Day 7-14 | — | 18539.6 | 3296.1 |
| | Day 14-21 | — | 11533.5 | 1791.2 |
| | Day 21-28 | — | 10696.4 | 1891.7 |

*Note:
The control group was the differentiation medium alone.

From the results of insulin content analysis listed in Table 2 above and FIG. 1, it was clearly known that the insulin secretion of the high secretion insulin-producing cells could reach the maximum value for 7 days during cell culture. And the insulin concentration of example 1 is obviously higher than the insulin concentration of example 2, which shows that the cell density is not proportional to the amount of insulin secreted by high secretion insulin-producing cells. The higher the cell density, the lower the insulin secretion.

Therefore, the following embodiments were all using $5 \times 10^5$ hADSCs in a T75 flask for differentiation.

Insulin Secretion Analysis

The above differentiation test (example 1) was repeat for 3 times and means of insulin secretion of each 100 thousand of high secretion insulin-producing cells every 7 days were calculated and recorded in Table 3.

TABLE 3

| Unit | Control (mIU/L) | Insulin secretion of each 100 thousand of the insulin-producing cells (mIU/L) |
| --- | --- | --- |
| Days 0-7 | 57.63 ± 51.15 | 10569.66 ± 4686.63 |
| Days 7-14 | — | 2526.02 ± 934.01 |
| Days 14-21 | — | 2290.09 ± 631.54 |
| Days 21-28 | — | 2409.42 ± 694.69 |

*Note:
The control group was the differentiation medium alone.

As shown in Table 3, the insulin secretion of the high secretion insulin-producing cells could reach the maximum value within 7 days during cell culture, and the insulin secretion of each $10^5$ high secretion insulin-producing cells was 10569.66 mIU/L. In other words, the average daily insulin secretion of each $10^5$ high secretion insulin-producing cells were about 1510 mIU/L.

Morphology of High Secretion Insulin-Producing Cells

At day 0 and day 7 during cell culture, the cells in the flask were photographed and observed respectively by an inverted microscope (model: OLYMPUS IX71-1LL100).

Figure 2:
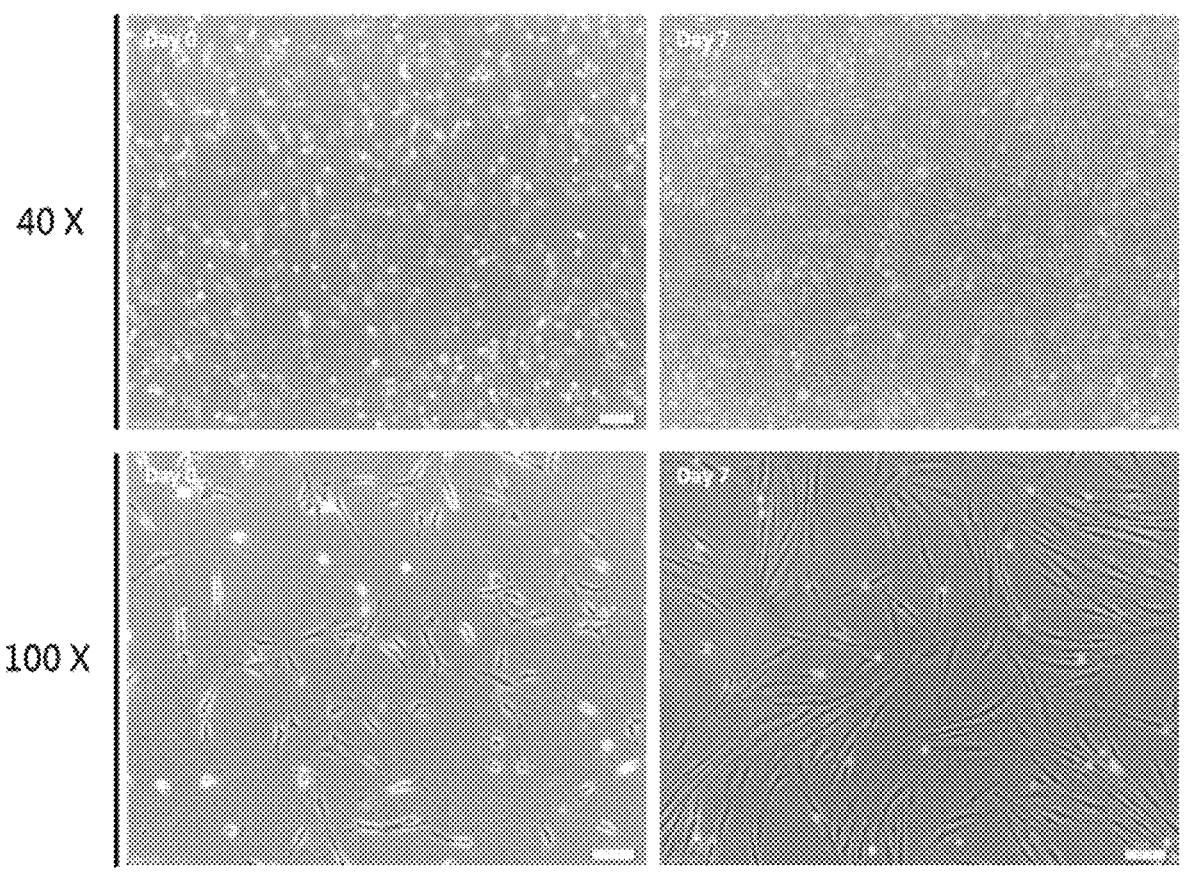
FIG. 2 is a diagram illustrating cell morphological changes at day 0 and day 7 during cell differentiation.

As shown in FIG. 2, during the differentiation, the morphology of high secretion insulin-producing cells was spindle-shaped, and all the high secretion insulin-producing cells are separated rather than aggregated into spheres or clumps.

Expression of Surface Markers of High Secretion Insulin-Producing Cells

The cells were collected at day 0 and day 7 during cell culture, and then they were fixed and dyed with each specific antibody for cell surface marker (negative marker: CD45; positive marker: CD73 and CD90). The surface antibody was labeled with FITC conjugated secondary antibody, and the fluorescent signal expression of the cell surface protein was measured using a flow cytometer (Model: BD Accuri C6). The analysis was repeated at least twice and the average values were recorded in Table 4.

TABLE 4

| | | Day 0 | Day 7 |
| --- | --- | --- | --- |
| Percentage of positive cells (normalized to isotype) | CD73 | 99.775 | 99.935 |
| | CD90 | 99.985 | 99.985 |
| | CD45 | 0.095 | 0.095 |

Figure 3A:
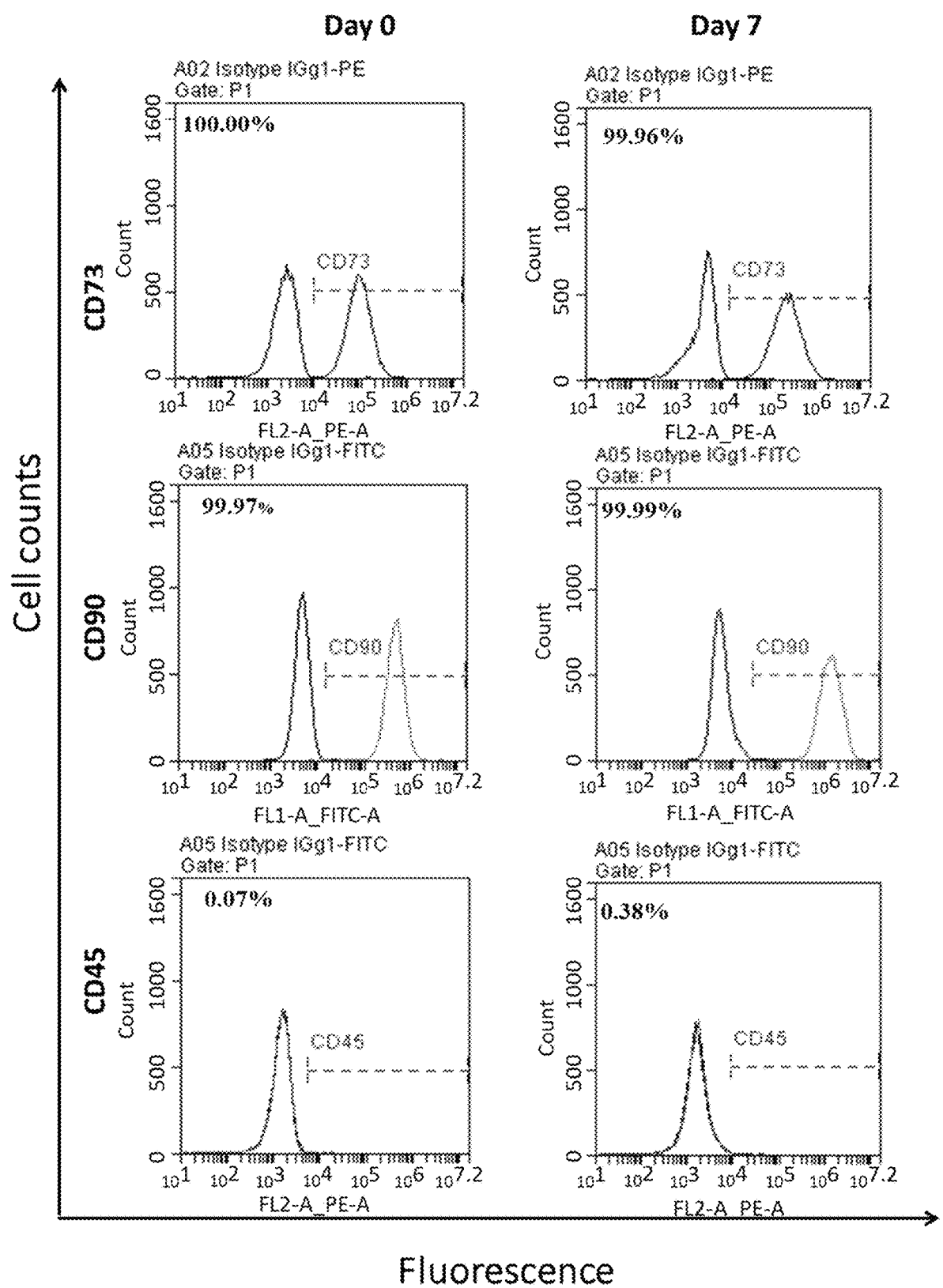
FIG. 3A is a diagram illustrating the results of the fluorescent signal expression of cell surface markers at day 0 and day 7 during cell differentiation.
Figure 3B:
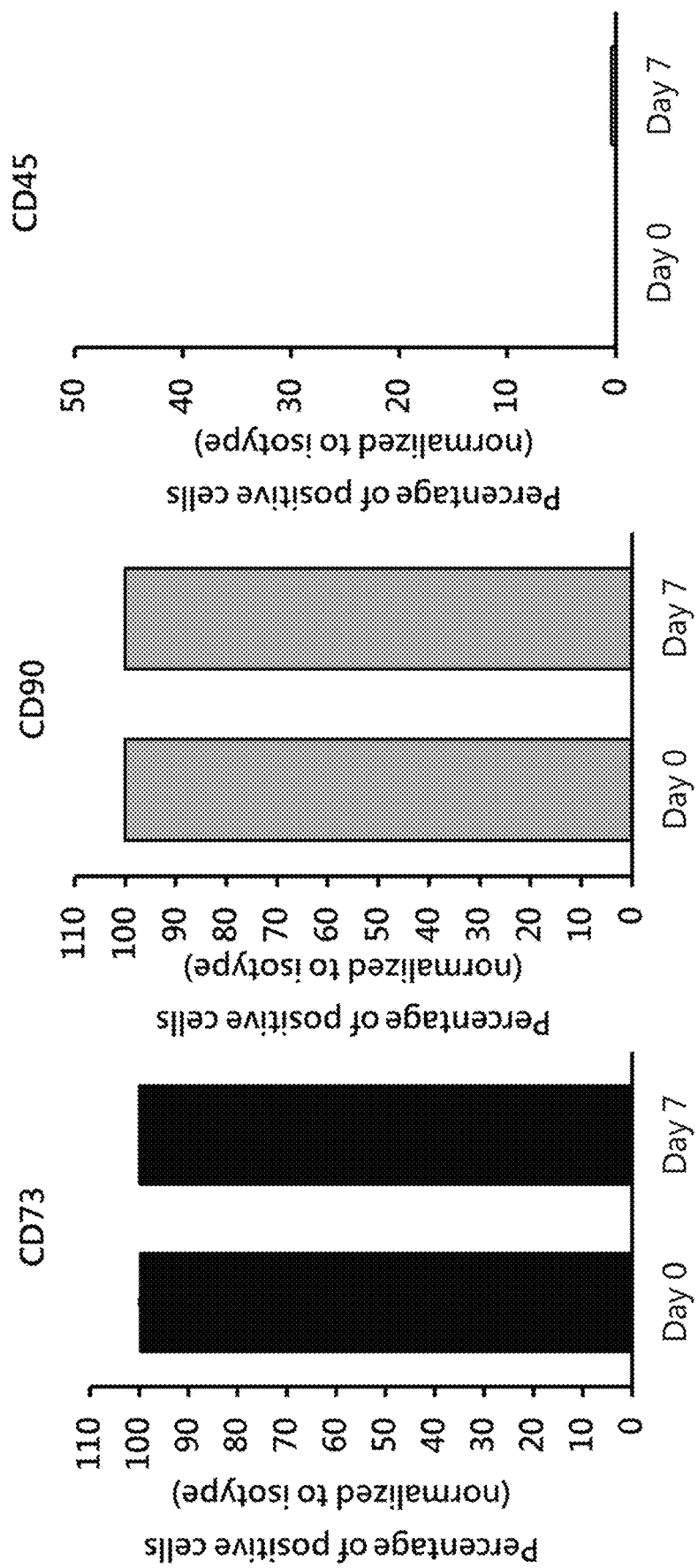
FIG. 3B is a diagram illustrating the normalized results of the expression of cell surface markers at day 0 and day 7 during cell differentiation.

As shown in Table 4, FIG. 3A and FIG. 3B, after 7 days during cell culture, the high secretion insulin-producing cells showed 0.095% for the negative markers CD45, whereas for CD 73 and CD90, the stem cell positive markers, were mostly found to be 99% or higher. In other words, the culturing conditions of the present invention did not change the expression of specific surface markers of high secretion insulin-producing cells, which was still the same with hADSCs (stem cells).

Gene Expression of High Secretion Insulin-Producing Cells

The cells were collected at day 0 and day 7 during cell culture. mRNA of the cells was isolated using mRNA isolation kits (Quick-RNAm MiniPrep, ZYMO RESEARCH), and then the isolated mRNA was reverse transcribed to cDNA using reverse transcription kit (PrimeScript™ RT reagent Kit, Takara). 100 ng of cDNA sample and proper primers for Insulin, Ipf-1, Isl-1, and CD47 were mixed with SYBR® Premix Ex Taq™ II (Takara) for Real time PCR.

The proper primers for Insulin, Ipf-1, Isl-1, and CD47 were shown in Table 5.

TABLE 5

| specific gene | Forward primer | Reverse primer |
|---|---|---|
| Ipf-1 | 5'-TGATACTGGATTGGCGT TGTTT-3' (SEQ ID NO: 1) | 5'-TCCCAAGGTGGAGTG CTGTAG-3' (SEQ ID NO: 2) |
| Isl-1 | 5'-CAACTGGTCAATTTTTC AGAAGGA-3' (SEQ ID NO: 3) | 5'-TTGAGAGGACATTGA TGCTACTTCAC-3' (SEQ ID NO: 4) |
| Insulin | 5'-GCAGCCTTTGTGAACCA ACA-3' (SEQ ID NO: 5) | 5'-TTCCCCGCACACTAG GTAGAGA-3' (SEQ ID NO: 6) |
| CD47 | 5'-GGCAATGACGAAGGAGG TTA-3' (SEQ ID NO: 7) | 5'-ATCCGGTGGTATGGA TGAGA-3' (SEQ ID NO: 8) |
| HPRT (reference gene) | 5'-TCAGGCAGTATAATCCA AAGATGGT-3' (SEQ ID NO: 9) | 5'-AGTCTGGCTTATATC CAACACTTCG-3' (SEQ ID NO: 10) |

After mRNA isolation, reverse transcription to cDNA and real-time PCR were done, each gene expression was analyzed and record in Table 6.

TABLE 6

| | | Day 0 | Day 7 |
|---|---|---|---|
| Relative mRNA expression (Normalized to HPRT mRNA) | Insulin | 1 | 11.47 |
| | Ipf-1 | 1 | 5.89 |
| | Isl-1 | 1 | 6.13 |
| | CD47 | 1 | 3.64 |

Figure 4:
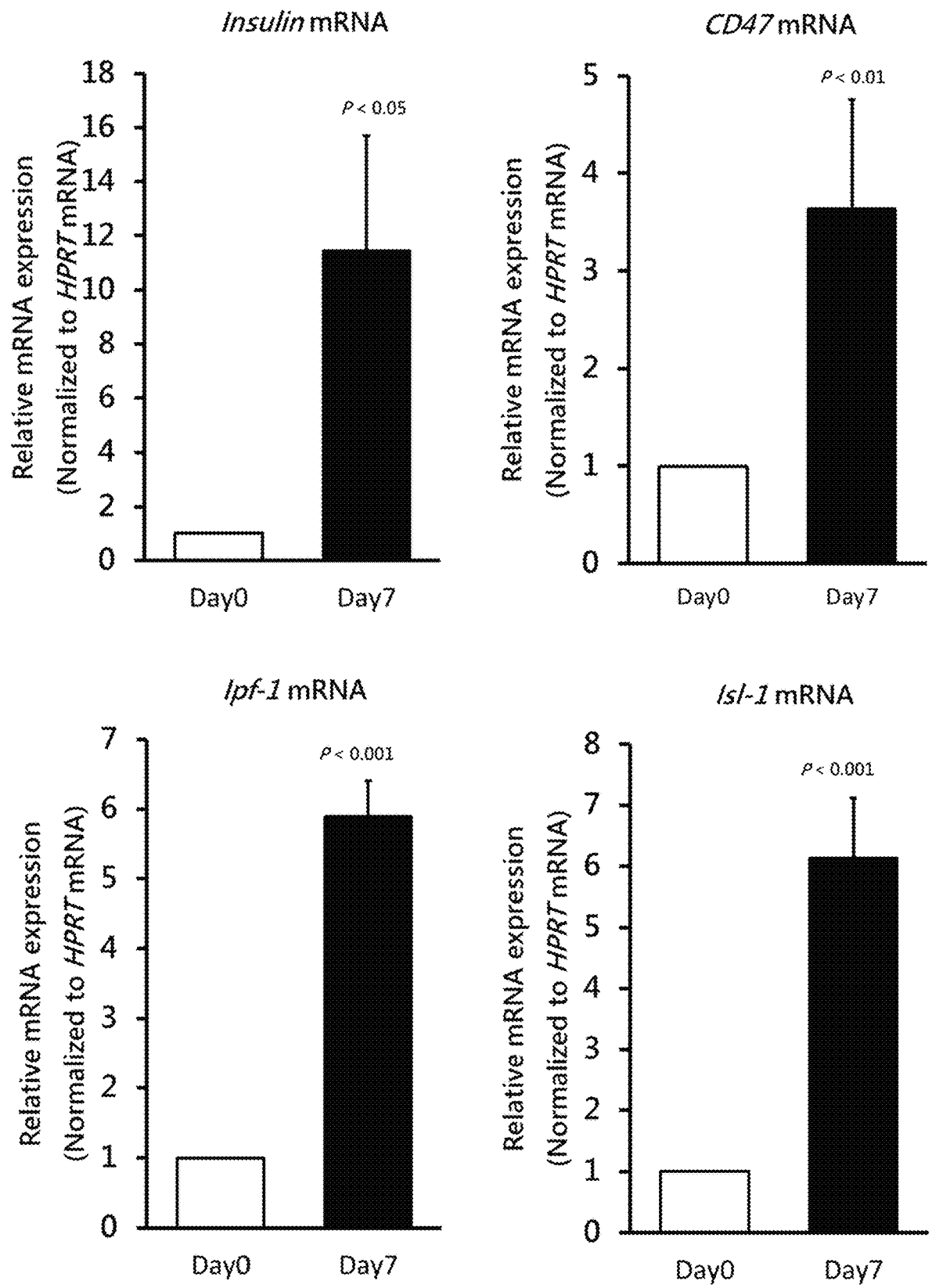
FIG. 4 is a diagram illustrating results of mRNA expression of cells at day 0 and day 7 during cell differentiation.

As shown in Table 6, FIG. 4, after 7 days during cell culture, the expressions of the Insulin gene, Ipf-1 gene, and Isl-1 gene in the high secretion insulin-producing cells were significantly increased to at least 5 times compared with hADSCs which had not begun to be differentiated at day 0.

In addition, the expressions of CD47 in the high secretion insulin-producing cells were also significantly increased to at least 3 times compared with hADSCs at day 0. Since CD47 is a signaling molecule prevents phagocytosis of Macrophages, the result in the analysis means the high secretion insulin-producing cells of the present invention could be avoid phagocytosis of Macrophages in human body when being used in human transplantation, thereby improving the survival rate of the high secretion insulin-producing cells.

It can be seen from the above-mentioned embodiments that the present invention provides a cell differentiation medium composition and a preparation method for the high secretion insulin-producing cell, which are cultured stem cells by monolayer culturing to prevent cells from aggregating into spheres or clumps. The present can not only facilitate collection cells and measurement, also can obtain a large amount of insulin in a short time, which is helpful for industrial utilization; and when the high secretion insulin-producing cells are transplanted into the human body, they are not easy to be swallowed by macrophages, which can extend the time of insulin secretion.

The specific embodiments described above are only used to illustrate the features and effects of the present invention, and are not intended to limit the implementation scope of present invention. Any equivalent changes and modifications made based on the content disclosed in the present invention without departing from the spirit and technical scope of the present invention still fall within the patent scope described later.

What is claimed is:

1. A preparation method for a high secretion insulin-producing cell, which comprises,
    (a) cell proliferation step: culturing stem cells at least 3 days for cell proliferation by using a proliferation medium; the proliferation medium consists of keratinocyte serum-free media, fetal bovine serum, N-acetyl-L-cysteine, L2 ascorbic acid, and phosphate;
    (b) cell attachment step: pour a solution containing the stem cells into a cell culture container and let stand for at least 24 hours for cell attachment, so that the quantity of stem cells attached to the peripheral wall of the culture container is in a range of 6,000 and 15,000 cells/cm$^2$;
    (c) cell differentiation step: removing the solution from the culture container, putting a cell differentiation medium composition into the culture container, inducing the stem cells into high-secreting insulin-producing cells under the conditions of an ambient temperature of 35.5~39.5° C. and a $CO_2$ concentration of 5%, and then collecting the high-secreting insulin-producing cells after differentiating for at least 2 days; wherein
    the cell differentiation medium composition is antibiotic-free and is a serum-free DMEM/F12 medium comprising at least 5~25 mM glucose, 5~15 mM nicotinamide, 1~10 μM activin-A, 5~20 nM exendin-4, 80~120 nM hepatocyte growth factor, 2~20 nM pentagastrin, and a 0.1~5% N-2 Supplement;
    the morphology of the high secretion insulin-producing cell is spindle-shaped; and
    the insulin secretion of each 100 thousand of the high secretion insulin-producing cells per day is above 1,000 mIU/L.

2. The preparation method for a high secretion insulin-producing cell according to claim 1, wherein cell culture time in the cell differentiation step (b) is in a range of 3 to 30 days.

3. The preparation method for a high secretion insulin-producing cell according to claim 1, wherein the stem cell is at least one selected from the group consisting of an adipose-derived stem cell, a bone marrow stem cell, a peripheral blood stem cell, a cord blood stem cell.

4. The preparation method for a high secretion insulin-producing cell according to claim 1, wherein the high secretion insulin-producing cell demonstrates positive expression of the genes insulin, IPF-1, and ISL-1.

5. The preparation method for a high secretion insulin-producing cell according to claim 4, wherein the high secretion insulin-producing cell demonstrate positive expression of CD73 and CD90, and negative expression of CD45, which are the same with the stem cells.

* * * * *